(12) United States Patent
Cole et al.

(10) Patent No.: US 6,306,386 B1
(45) Date of Patent: Oct. 23, 2001

(54) BIOLOGICAL CONTROL FORMULATIONS CONTAINING SPORES OF NONTOXIGENIC STRAINS OF FUNGI FOR TOXIN CONTROL OF FOOD CROPS

(75) Inventors: Richard J. Cole; Joe W. Dorner, both of Albany, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/621,466

(22) Filed: Jul. 21, 2000

Related U.S. Application Data

(60) Provisional application No. 60/145,251, filed on Jul. 26, 1999.

(51) Int. Cl.$^7$ ............................. A01N 63/00; A01N 25/00
(52) U.S. Cl. ..................... 424/93.1; 424/93.5; 424/405
(58) Field of Search .................. 424/93.1, 93.5, 424/405, 408, 410, 417, 439

(56) References Cited

U.S. PATENT DOCUMENTS

| | | | |
|---|---|---|---|
| 4,925,663 | * 5/1990 | Stimac | 424/93 |
| 5,171,686 | 12/1992 | Cotty et al. | 435/254 |
| 5,292,661 | 3/1994 | Cole et al. | 435/267 |
| 5,294,442 | * 3/1994 | Cotty | 424/93 |
| 5,413,784 | 5/1995 | Wright et al. | 424/93.5 |
| 5,730,973 | 3/1998 | Morales et al. | 424/93.5 |

OTHER PUBLICATIONS

Dorner, J., et al., "The Relationship of *Aspergillus flavus* and *Aspergillus parasiticus* with Reference to Production of Aflatoxins and Cyclopiazonic Acid", *Mycopathologia*, vol. 87, pp. 13–15, 1984.

Schmidt, F., et al., "Viral Influences on Aflatoxin Formation by *Aspergillus flavus*", *Appl. Microbiol. Biotechnol.*, vol. 24. pp. 248–252, 1986.

Jishen, S., et al., "Electron Microscopy Study of Toxigenic and Non–Toxigenic Strains of Fungi *Aspergillus Flavus* ", *ACTA Academiae Medicinae Sinicae*, vol. 8, (1), p. 71, Feb. 1986.

Lemke, P., et al., "Direct Visual Detection of Aflatoxin Synthesis by Minicolonies of Aspergillus Species", *Appl. Environ. Microbiol.*, vol. 55, (7), pp. 1808–1810, Jul. 1989.

Lee, L.S., "Metabolic Precursor Regulation of Aflatoxin Formation in Toxigenic and Non–Toxigenic Strains of *Aspergillus flavus*", *Mycopathologia*, vol. 107, pp. 127–130, 1989.

Dorner, J., et al., "Use of a Biocompetitive Agent to Control Preharvest Aflatoxin in Drought Stressed Peanuts", *J. Food Prot.*, vol. 55, (11), pp. 888–892, Nov. 1992.

Tantaoui–Elaraki, A., "Selection for More Toxigenic Son–Thalli or Less Aflatoxin–Producing Son–Thalli Starting from a Mother–Colony of *Aspergillus flavus*", *J. Environ. Path.,Toxic. and Oncol.*, vol. 11, (2), pp. 97–101, 1992.

Horn, B., et al., "Association of Morphology and Mycotoxin Production with Vegetative Compatibility Groups in *Aspergillus flavus*, A. parasiticus, and A. tamarii", *Mycologia*, vol. 88, (4), pp. 574–587, 1996.

* cited by examiner

*Primary Examiner*—Jon P. Weber
*Assistant Examiner*—Patricia Patten
(74) *Attorney, Agent, or Firm*—M. Howard Silverstein; John D. Fado; Gail E. Poulos

(57) ABSTRACT

Formulations containing spores of non-toxigenic strains of fungi are useful biocontrol agents for preventing toxin contamination in agricultural commodities, especially those for human and animal consumption such as peanuts, corn and cotton. These formulations include spores mixed with vegetable oil and applied to dry grain. Diatomaceous earth is added to the spore, oil and grain mixture to form a flowable formulation.

9 Claims, No Drawings

BIOLOGICAL CONTROL FORMULATIONS CONTAINING SPORES OF NONTOXIGENIC STRAINS OF FUNGI FOR TOXIN CONTROL OF FOOD CROPS

This application claims benefit of copending provisional application Ser. No. 60/145,251 filed Jul. 26, 1999.

BACKGROUND OF THE INVENTION

1. Field of the Invention

The present invention relates to a biocontrol formulation for delivering non-toxigenic strains of fungi, such as for example, Aspergillus including *Aspergillus flavus* (*A. flavus*), *Aspergillus parasiticus* (*A. parasiticus*), *Aspergillus oryzae* (*A. oryzae*), and *Aspergillus sojae* (*A. sojae*) to crops in methods for the control of toxin contamination in agricultural commodities. The present invention also relates to a method for preparing the biocontrol formulations. This invention claims priority of United States Provisional Patent Application 60/145,251 filed Jul. 26, 1999; which is herein incorporated by reference.

2. Description of the Related Art

Aflatoxins are potent hepatotoxic, carcinogenic compounds produced by *A. flavus* Link:Fr. and *A. parasiticus* Speare (CAST, In: Mycotoxins: Economic and Health Risks. Report 116, 99 pp., Council for Agricultural Science and Technology, 137 Lynn Avenue, Ames, IA 50010). Cyclopiazonic acid (CPA) is another potent mycotoxin that is produced by *A. flavus*, but not by *A. parasiticus*. When these fungi invade and grow in commodities such as peanuts, corn, cottonseed, and tree nuts, the resulting contamination with the aflatoxins and CPA often makes the commodity unfit for consumption. The United States peanut industry has identified aflatoxin contamination of peanuts as the number one problem for which a solution is needed (Consensus Report of the National Peanut Council Quality Task Force, 1987, National Peanut Council, Alexandria, Va. 22314). Because peanuts are used primarily for food, strict regulatory limits for the amount of aflatoxin allowable in finished peanut products have been established. Although the United States Food and Drug Administration has an action level of 20 ppb of total aflatoxins in food products, international tolerances for aflatoxin are much lower, typically in the range of 0–4 ppb, and are important because U. S. companies compete internationally in the market to export peanuts and peanut products. For this reason the United States peanut industry has a goal to ensure the delivery of aflatoxin-free peanut products by the year 2000. Although aflatoxin contamination of peanuts can occur during post-harvest curing and storage, the most significant contamination usually occurs prior to harvest during periods of late-season drought stress as peanuts are maturing. The only known method for controlling preharvest aflatoxin contamination in peanuts is irrigation, an option that is unavailable to the majority of peanut growers.

Cyclopiazonic acid is an indole-tetramic acid that was first isolated from cultures of *Penicillium cyclopium* Westling in 1968 (Holzapfel, Tetrahedron,Volume 24, 2101–2119, 1968). CPA is now know to be produced by a variety of fungi including *P. patulum, P. viridicatum, P. puberulum, P. crustosum, P. cainemberti, A. flavus, A. versicolor* and *A. oryzae*. In addition, CPA has been found as a natural contaminant of corn and peanuts, often occurring together with aflatoxin (Lansden and Davidson, Applied and Environmental Microbiology, Volume 45, 766–769,1983; Urano et al., Journal of AOAC International, Volume 7S, 838–841, 1992). It was also implicated as the causative agent in a human intoxication involving consumption of contaminated millet (Rao and Husain, Mycopathologia, Volume 89, 177–180, 1985). With the discovery of CPA production by *A. flavus*, 54 isolates of *A. flavus* were investigated for production of CPA and aflatoxin (Gallagher et al., Mycopathologia, Volume 66, 31–36, 1978). It was found that 28 of the 54 (52%) produced CPA whereas only 18 (33%) produced aflatoxin. Regulatory limits for CPA have not been established; however, because of the co-occurrence of aflatoxin and CPA in commodities, efforts to attain biological control of aflatoxin also need to attain control of CPA.

It has been previously found that co-cultivation of either *A. parasiticus* or *A. flavus* with species of Penicillium reduce levels of aflatoxin production while co-cultivation of Fusarium species had no such effect (Ehrlich et al., Experiential, Volume 41, 691–693, 1985). These tests did not involve the use of a soil environment. Co-cultivation with A. niger completely eliminated the production of aflatoxin by a culture of *A. flavus* (Wicklow et al., Phytopathology, Volume 70, 761–764, 1980). This testing was done under laboratory controlled conditions in which the food source involved sterilized corn.

The conventional method for producing biocontrol formulations for aflatoxin control is via solid state fermentation (SSF) using a suitable substrate such as wheat or rice (Bock and Cotty, Biocontrol Science and Technology, Volume 9, 529–543, 1999). It is necessary to rehydrate, sterilize, inoculate and ferment the substrate with the biocontrol organism (s) and dry the formulation to a safe moisture level. Scale-up of the SSF method is difficult since manufacturing facilities are currently not available. The SSF method is not cost effective and also has potential safety problems since some spores are produced that can become airborne during manufacture and field application.

Cotty (U.S. Pat. No. 5,171,686-Dec. 15, 1992 and U.S. Pat. No. 5,294,442-Mar. 15, 1994) discloses a non-toxigenic strain of *A. flavus* which inhibits aflatoxin production by toxigenic strains. Formulations for field delivery were prepared using the SSF method. The patent teaches that agricultural commodities inoculated simultaneously with both a non-toxigenic strain and a toxigenic strain produce seed with up to 100-fold less aflatoxin than commodities inoculated with a toxigenic strain alone.

Cole et al.(U.S. Pat. No. 5,292,661-Mar. 8, 1994) and Dorner et al.(Journal of Food Protection, Volume 55, 888–892, 1992) disclose a non-aflatoxigenic strain of *A. parasiticus*. The biocompetitive agent was prepared by growing the strains in 2.8 liter Fernbach flasks on liquid YES medium containing 15% sucrose, 5% mycological broth, pH 4.8, and 2% yeast extract; for two weeks at 27° C. Contents of the flasks were combined and homogenized in water plus 0.05% Tween 20. The homogenate was strained and applied over rows of peanuts using a garden sprinkler. The references teach the use of this strain as a biocontrol agent which reduces aflatoxin contamination of soilborne crops.

U.S. Pat. No. 5,730,973 (Morales et al., Mar. 24, 1998) discloses a biocontrol formulation containing 5–8% by weight of spores or active units of a fungus, 5–60% by weight of one or more suitable wetting agents and dispersants, 2–20% by weight of at least one protective substance which prevents desiccation which can include vegetable oil, 5–70% by weight of magnesium silicate or aluminum silicate, 0.5–20% by weight of at least one substance which protects against UV radiation, and a residual amount of water content at about 2–10%. The formulation is water dispersable and useful for the control of insect pests.

U.S. Pat. No. 5,413,784 (Wright et al., May 9, 1995) discloses a biopesticide which includes entomophathogenic fungi having virulence against targeted insect pests, an arrestant and feeding stimulant and optionally a pheromone. The feeding stimulant is defined as a combination of protein, carbohydrates, and lipid oil which can be formulated as a dispersable granule.

While various biocontrol formulations for control of toxigenic fungi are known in the art, there still remains a need for an effective biocontrol formulation for controlling toxigenic fungi. The present invention described below includes formulations and methods of preparing formulations that includes non-toxigenic strains of fungi which displace toxigenic fungi. The present invention also provides a method for controlling toxigenic fungi in agricultural crops which is different from the related art biocontrol methods

SUMMARY OF THE INVENTION

It is therefore, an object of the present invention to provide a formulation containing biocontrol agents for the control of toxigenic fungi in plants.

Another object of the present invention is to provide a biocontrol formulation containing non-toxigenic spores of fungi for preventing contamination of crops with toxin-producing fungi wherein said formulation contains spores dispersed in oil, applied to grain, and mixed with a silicate or a siliceous material such as diatomaceous earth to form a flowable formulation.

A further object of the present invention is to provide a method for biocontrol of toxin-producing fungi in plants using the disclosed biocontrol formulation A still further object of the present invention is to provide a method for producing formulations of non-toxin producing fungi which includes dispersing non-toxigenic spores of fungi in oil to form a first mixture, applying the first mixture to dry grain to form a second mixture, and mixing the second mixture with a silicate or siliceous material such as diatomaceous earth to form a flowable formulation.

A further object of the present invention is to provide a biocontrol method for peanuts, corn and cotton, which includes applying biocontrol formulations containing spores of fungal strains; wherein said formulation contains spores dispersed in oil, applied to grain, and mixed with a silicate or a siliceous material such as diatomaceous earth to form a flowable formulation.

Further objects and advantages of the present invention will become apparent from the following description.

DEPOSIT OF THE MICROORGANISMS

*Aspergillus flavus*, designated NRRL 21882 and NRRL 21368; *A. parasiticus*, designated NRRL 21369; have been deposited under the provisions of the Budapest Treaty on Nov. 12, 1997 (NRRL 21882); Dec. 8, 1994 (NRRL 21368 and NRRL 21369) with the U.S.D.A. Agricultural Research Service Patent Culture Collection (National Center for Agricultural Utilization Research, 1815 N. University Street, Peoria, Ill., 61604). *Aspergillus oryzae* strain 8–03, designated NRRL 30038, and *Aspergillus sojae* strain S-12, designated NRRL 30039, have been deposited on Jul. 2, 1998 under the provisions of the Budapest Treaty with the U.S.D.A. Agricultural Research Service Patent Culture Collection (National Center for Agricultural Utilization Research, 1815 N. University Street, Peoria, Ill., 61604).

DETAILED DESCRIPTION OF THE INVENTION

The addition of highly competitive, non-toxigenic fungal strains of *A. flavus, A. parasiticus, A. orzae*, and *A. sojae*, as well as mixtures of any of the strains, to soil results in lower concentrations of toxins in agricultural commodities. The non-toxigenic strains of Aspergillus become biocompetitive with the soil microflora and prevent buildup of toxin-producing strains that normally occurs during late-season drought, Through biocompetition, the toxigenic strains of fungi found naturally in soil, would be replaced by non-toxigenic strains added to the soil. Therefore, any crop subjected to late-season drought stress would be invaded predominately by the biocompetitive strains which are unable to produce toxins (U.S. patent application Ser. No. 09/110,132, filed Jul. 6, 1998; now U.S. Pat. No. 6,027,724, issued Feb. 22, 2000; herein incorporated by reference). The formulations and methods of the invention are applicable to any agricultrual commodity which is grown for human and/or animal consumption and/or which is damaged by fungal toxins such as for example peanuts, corn, cotton, etc.

For purposes of this invention, a fungal preparation or fungal agricultural biocontrol formulation refers to a microbial preparation wherein microbes comprise, consist essentially of, or consist of non-toxigenic strains of fungal spores of, for example, Aspergillus. Non-toxigenic strains include any fungus which does not produce toxins such as aflatoxin, cyclopiazonic acid (CPA) or both.

The method of the invention produces a simple, efficient, safe, less costly formulation for delivery of biocontrol organisms to fields to reduce preharvest aflatoxin contamination of crops. The method includes the steps of mixing spores with vegetable oil to form a first mixture followed by coating a substrate with the first mixture to form a second mixture. The second mixture is mixed with a silicate or a siliceous material such as diatomaceous earth to form a free flowing formulation which can be directly applied to soil. For purposes of the present invention, substrate is defined as any dry grain which does not have hull or bran, such as, for example, hulled barley or rice. Vegetable oil includes, for example, soybean, canola, peanut, corn, cottonseed, rapeseed, sunflower, etc. Silicates include, for example, any substance containing silicon, oxygen, and one or more metals without hydrogen. Examples of useful silicates would be any one which is useful on agricultural commodities, non-toxic to the biocontrol fungi, and would not cause environmental damage. Example of silicates include magnesium silicate, aluminum silicate, talc, clays, calcium silicate, etc. Siliceous materials include diatomaceous earth for example. Most preferred in the present invention is diatomaceous earth.

Spores of biocontrol fungi can be prepared using any known technique. Alternatively, dry spores can be purchased. A spore suspension is prepared by suspending spores of the fungus to be used as the biocontrol organism in an oil. A spore suspension containing from about $5 \times 10^7$ to about $1 \times 10^9$ CFU/gram, pref erabably about $1 \times 10^8$ CFU/g of spores in oil is prepared by suspending the spores in the oil at a rate of about 1 gram of spores per 100 grams of oil to form a first mixture. The spore-oil mixture is uniformly sprayed onto the surface of a grain, such as, for example, hulled barley, at a rate of approximately 1.5% (i.e., about 1.5 grams of oil-spore suspension per about 100 grams of grain).

This can be done in any suitable seed coating device, such as for example, a Cimbria Heid Centricoater, to produce a second mixture, which has an oily, sticky consistency. A silcate or siliceous material, such as, for example, diatomaceous earth, is then added at a rate of about 2.5 to about 3.0% (approximately 2.5 to 3.0 grams of diatomaceous earth per approximately 100 grams of coated grain) to the second mixture to produce a free-flowing biocontrol formulation. Use of the above preferred ratios of materials results in grain containing at least about $1 \times 10^5$ to about $5 \times 10^6$ CFU/gram, preferably about $5-10^5$ CFU/gram.

The formulation should be stored in an airtight container at room temperature to prevent uptake of moisture and has a shelf life of at least about 6 months with very little, if any, loss of spore viability.

The substrate grain does not have to be rehydrated or sterilized and the product formulation does not have to be dried. This method can be used in preparing biocontrol formulations using any fungus which produces spores.

The formulation is applied to the field in amounts effective to reduce toxin levels in agricultural commodities. As used herein "reduce toxin levels" refers to a reduction in amounts of toxin compared to that which would be expected in agricultural commodities which were not treated according to the methods of the present invention. Any accurate method of measuring and comparing toxin levels may be used for such comparisons, as would be apparent to those skilled in the art. As used herein "in amounts effective, or "an effective amount" refer to the amount of the fungal formulation administered wherein the effect of the administration acts to reduce toxin contamination of agricultural commodities. For example, the free-flowing formulation can be applied to the soil at a rate of about 20–900 pounds per acre, with 20–200 pounds preferred, and 20–50 pounds per acre most preferred, when the foliage canopy is about 12 inches wide. The soil surface under the canopy provides a humid, protected environment which promotes the growth and sporulation of the biocontrol fungi. The strains can be applied as single strain formulations or the dried products can be mixed in about equal proportions to provide a composition made up of different strains of biocontrol fungi.

The following examples are intended to further illustrate the invention and is not intended to limit the scope of the invention as defined by the claims.

EXAMPLE 1

Formulations were prepared with wheat and pearled barley using *Aspergillus flavus* (NRRL 21882). Approximately 6.25 grams of spores were suspended in about 1 liter of sunflower oil to form a spore suspension (first mixture). The spore-oil suspension was sprayed completely on about 50 pounds of dry wheat or pearled barley which is being continually mixed in a cement mixture as it is being sprayed to form a second mixture. Two pounds of diatomaceous earth was added with continual mixing to produce a free flowing biocontrol formulation.

Alternatively, *A. flavus* (NRRL 21882) was cultured on sterile wheat to produce a formulation by the SSF method in the following manner. About 100 grams of wheat was placed in an Erlenmeyer flask and about 7 mL distilled water was added. The wheat was allowed to imbibe water while mixing for about 20 minutes. The imbibed wheat was sterilized in an autoclave for about 60 minutes and then allowed to cool. About 15 mL of approximately $1 \times 10^6$ conidia/ml spore suspension of NRRL 21882 was added to the flask and incubated for about 24 hours. The wheat was then dried at about 60° C. overnight.

The wheat formulation produced by SSF was compared with formulations of wheat and pearled barley by the coating process of the present invention to determine the amount of secondary spore production that would occur when conditions for fungal growth existed, such as after the inoculum would be applied to soil. Kernels of grain prepared by each method were placed on moist paper towels in Petri dishes and incubated for about eight days at about 30° C. After fungi grew on the kernels, they were homogenized in about 0.2% agar water with Tween 20 to produce a spore suspension. Dilution platings were carried out to determine the colony forming units (CFU) produced per gram of grain. Results in Table 1 below illustrate that the coating process yielded secondary spore production that was equal to or greater than that produced by the SSF method.

TABLE 1

Secondary spore production (CFU/g) of biocontrol formulations prepared by the SSF method and by the method of the present invention.

| FORMULATION | CFU/g |
| --- | --- |
| SSF Wheat | $1.9 \times 10^9$ |
| Coated Wheat | $2.3 \times 10^9$ |
| Coated Pearled Barley | $3.6 \times 10^9$ |

EXAMPLE 2

Field studies were conducted in 1999 to compare the efficacy of formulations prepared by the SSF method with formulations prepared by the coating process of the present invention. Sterile rice was colonized with nontoxigenic strains of *A. flavus*(NRRL 21882) and *A. parasiticus* (NRRL 21369) by the SSF method as described for wheat in example 1. Rice and hulled barley were also prepared with the same fungi using the coating process as in Example 1. Each of the three formulations containing a mixture of the two fungal species was applied to 16 peanut plots (6 rows×50 feet) at 78 days after planting at a rate of 50 pounds per acre. Sixteen non-inoculated plots served as controls. Peanuts were exposed to late season drought conditions that were conducive for aflatoxin contamination. The middle two rows of each plot were harvested and all peanuts were ground in a vertical cutter mixer and analyzed for aflatoxin by HPLC. Results appearing in Table 2 below showed that all three formulations produced statistically significant reductions in aflatoxin contamination compared with controls. Results of treatment with the different formulations were not significantly different, and the recommended formulation containing hulled barley produced an 80.5% reduction in aflatoxin compared with controls.

TABLE 2

Mean aflatoxin concentrations in peanuts from plots treated with three different biological control formulations

| TREATMENT | AFLATOXIN (ppb) | % REDUCTION |
| --- | --- | --- |
| Control | 673.1a | |
| SSF Rice | 90.1b | 86.6 |
| Coated Rice | 154.5b | 77.0 |
| Coated Hulled Barley | 130.6b | 80.5 |

Means in a column followed by the same letter are not significantly different ($p < 0.01$)

EXAMPLE 3

Additional field studies were conducted in 1999 in which a mixture of formulations prepared using the coating process containing nontoxigenic strains of *A. flavus* (NRRL 21882) and *A. parasiticus* (NRRL 21369) was applied to six 2.5 acre (24 rows×about 150 feet) peanut plots at 67 days after planting. The formulation mixture was applied at a rate of about 20 pounds per acre. Equivalent plots that were not treated served as controls. Peanuts were exposed to late season drought conditions conducive for the development of aflatoxin contamination.

Soil samples taken from each plot at harvest showed a dominance of the applied strains over naturally occurring wild-type strains. Total populations of *A. flavus* and *A. parasiticus* in control plots averaged about 3058 CFU/g with about 99% of the srains found to be wild-type strains. Total populations of *A. flavus* and *A. parasiticus* in treated plots averaged 6833 CFU/g with >99% being the applied strains. When soil samples from these plots were rechecked in April 2000, total populations averaged about 2245 and 1725 CFU/g for control and treated plots, respectively. Treated plot populations were still heavily (>99%) dominated by the biocontrol strains that had been applied. However, total *A. flavus* and *A. parasiticus* soil populations were not significantly ($p<0.05$) different.

Peanut samples from each plot taken at harvest showed that peanuts from plots treated with the biocontrol formulation contained an average aflatoxin concentration of about 54.1 ppb compared with about 516.8 ppb in peanuts from the control plots. This was a statistically significant ($p<0.01$) reduction of about 89.5% in aflatoxin contamination resulting from treatment with the biocontrol formulation.

The foregoing detailed description is for the purpose of illustration. Such detail is solely for that purpose and those skilled in the art can make variations therein without departing from the spirit and scope of the invention.

What is claimed is:

1. A non-toxigenic biocontrol formulation comprising spores of a fungal strain wherein said formulation is prepared by a process consisting essentially of:

(a) suspending an effective amount of a non-toxigenic fungi for biological control in a vegetable oil to form a first mixture, (b) adding a dry grain to said first mixture to form a second mixture, and (c) mixing said second mixture with a silicate or siliceous material to form a flowable biocontrol formulation.

2. A method for reducing toxin contamination of agricultural commodities comprising applying to said commodities, a biocontrol formulation prepared by the process of:

(a) suspending an effective amount of an Aspergillus strain selected from the group consisting of *Aspergillus oryzae, Aspergillus flavus, Aspergillus parisiticus, Aspergillus Sojae*, and mixtures thereof in vegetable oil to form a first mixture;

(b) adding a dry grain to the first mixture of part (a) to form a second mixture; and (c) mixing said second mixture of part (b) with a silicate or siliceous material to form a flowable biocontrol formulation, wherein said biocontrol strains do not produce aflatoxin, bis-furan ring-containing intermediates of the aflatoxin biosynthetic pathway or cyclopiazonic acid.

3. The method of claim 2 wherein said vegetable oil is selected from the group consisting of soybean oil, canola oil, peanut oil, corn oil, rapeseed oil, sunflower oil, and mixtures thereof.

4. The method of claim 2 wherein said agricultural commodities are selected from the group consisting of peanuts, corn, cotton, and tree nuts.

5. The method of claim 2 wherein dry grain is selected from the group consisting of barley, wheat, oats, rice, rye, and mixtures thereof.

6. A method for preparing a flowable biocontrol formulation consisting essentially of:

(A) suspending spores of a nontoxigenic fungi in a vegetable oil to form a first mixture, (B) adding a dry grain to said first mixture to form a second mixture, and (C) mixing said second mixture with a silicate or siliceous material to form a flowable biocontrol formulation.

7. The method of claim 6 wherein said dry grain is a grain containing no hull or bran.

8. The method of claim 6 wherein said vegetable oil is selected from the group consisting of soybean oil, canola oil, peanut oil, corn oil, rapeseed oil, sunflower oil, and mixtures thereof.

9. The method of claim 6 wherein said silicate or siliceous material is selected from the group consisting of magnesium silicate, aluminum silicate, talc, clays, calcium silicate, diatomaceous earth and mixtures thereof.

* * * * *